(12) United States Patent
Peduto et al.

(10) Patent No.: US 11,780,934 B2
(45) Date of Patent: Oct. 10, 2023

(54) USE OF INHIBITORS OF ADAM12 AS ADJUVANTS IN TUMOR THERAPIES

(71) Applicants: INSTITUT PASTEUR, Paris (FR); INSTITUT NATIONAL DE LA SANTE ET DE LA RECHERCHE MEDICALE, Paris (FR)

(72) Inventors: Lucie Peduto, Paris (FR); Selene Di Carlo, Paris (FR)

(73) Assignees: INSTITUT PASTEUR, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 16/073,777

(22) PCT Filed: Feb. 3, 2017

(86) PCT No.: PCT/EP2017/052453
§ 371 (c)(1),
(2) Date: Jul. 28, 2018

(87) PCT Pub. No.: WO2017/134265
PCT Pub. Date: Aug. 10, 2017

(65) Prior Publication Data
US 2019/0031776 A1 Jan. 31, 2019

Related U.S. Application Data

(60) Provisional application No. 62/291,656, filed on Feb. 5, 2016.

(51) Int. Cl.
| | |
|---|---|
| *A61K 39/395* | (2006.01) |
| *C07K 16/40* | (2006.01) |
| *A01K 67/027* | (2006.01) |
| *A61K 45/06* | (2006.01) |
| *A61K 39/00* | (2006.01) |

(52) U.S. Cl.
CPC .......... *C07K 16/40* (2013.01); *A01K 67/0275* (2013.01); *A61K 39/3955* (2013.01); *A61K 45/06* (2013.01); *A01K 2217/052* (2013.01); *A01K 2217/30* (2013.01); *A01K 2227/105* (2013.01); *A01K 2267/0331* (2013.01); *A01K 2267/0393* (2013.01); *A61K 2039/505* (2013.01); *A61K 2039/585* (2013.01)

(58) Field of Classification Search
None
See application file for complete search history.

(56) References Cited

U.S. PATENT DOCUMENTS

| | | | |
|---|---|---|---|
| 2012/0225082 A1* | 9/2012 | Peduto | A61K 38/4886 424/158.1 |
| 2014/0099340 A1 | 4/2014 | June et al. | |

FOREIGN PATENT DOCUMENTS

| | | |
|---|---|---|
| WO | WO 2006/014903 A2 | 2/2006 |
| WO | 2009/111507 A1 | 9/2009 |
| WO | WO 2011024146 A2 | 3/2011 |
| WO | WO 2015/028027 A1 | 3/2015 |

OTHER PUBLICATIONS

Shimura et al. Suppression of proHB-EGF Carboxy-Terminal Fragment Nuclear Translocation: A New MolecularTargetTherapy for Gastric Cancer. Clin Cancer Res 2008;14(12):3956. (Year: 2008).*
Jacobsen and Wewer. Targeting ADAM12 in Human Disease: Head, Body or Tail? Curr Pharm Des. 2009;15(20):2300-10. (Year: 2009).*
Duhachek-Muggy and Zolkiewska. ADAM12-L is a direct target of the miR-29 and miR-200 families in breast cancer. BMC Cancer (2015) 15:93. (Year: 2015).*
Kveiborg et al. Selective inhibition of ADAM 12 catalytic activity through engineering of tissue inhibitor of metalloproteinase 2 (TIMP-2). Biochem J. Aug. 15, 2010; 430(1): 79-86. (Year: 2010).*
Nyren-Erickson et al. A disintegrin and metalloproteinase-12 (ADAM12): Function, roles in disease progression, and clinical implications. Biochimica et Biophysics Acts 1830 (2013) 4445-4455. (Year: 2013).*
Roy and Moses. ADAM 12: A novel mediatoroftumor Angiogenesis. Abstract 5285. Proceedings: AACR 103rd Annual Meeting 2012. (Year: 2012).*
Rao et al. A positive feedback loop between HER2 and ADAM12 in human head and neck cancer cells increases migration and invasion. Oncogene (2012) 31, 2888-2898. (Year: 2012).*

(Continued)

*Primary Examiner* — Maher M Haddad
(74) *Attorney, Agent, or Firm* — Arrigo, Lee, Guttman & Mouta-Bellum LLP

(57) ABSTRACT

It has been discovered that disrupting the stromal capsule restores a better vasculature/tumor perfusion and improve T cells infiltration inside the core of a melanoma. The invention relates to the use of drugs or immunoconjugates that target the transmembrane protease ADAM12 and deplete the cells that express it. Since ADAM12 protein is specifically expressed by stromal cells of the tumor stromal capsule and around vessels in models for prostate cancer, neuroendocrine pancreatic cancer and melanoma, an ADAM12 inhibitor is useful in anti-tumor therapies as an adjuvant. The invention encompasses methods, compositions, and kits containing ADAM12 inhibitors for use in the depletion of ADAM12+ stromal cells in cancer patient, particularly together with anti-tumor compounds and treatments.

21 Claims, 7 Drawing Sheets

(56) References Cited

OTHER PUBLICATIONS

Roy et al. ADAM 12 Is a Novel Regulator of Tumor Angiogenesis via STAT3 Signaling. Mol Cancer Res; 1-15, 2017. (Year: 2017).*

Shao et al. ADAM-12 as a Diagnostic Marker for the Proliferation, Migration and Invasion in Patients with Small Cell Lung Cancer. PLoS ONE 9(1): e85936. (Year: 2014).*

Narita et al Molecular profiling of ADAM12 gene in breast cancers. Romanian Journal of morphology and Embryology, 2010, 51(4): 669-676. (Year: 2010).*

Dulauroy et al Lineage tracing and genetic ablation of ADAM12+ perivascular cells identify a major source of profibrotic cells during acute tissue injury. Nature Medicine vol. 18, pp. 1262-1270(2012). (Year: 2012).*

Fang et al. A potent immunotoxin targeting fibroblast activation protein for treatment of breast cancer in mice. Int. J. Cancer: 138, 1013-1023 (2016). (Year: 2016).*

Provenzano et al. Enzymatc targeting ot the stroma ablates physical barriers to treatment or pancreatic ductal adenocarcinoma. Cancer Cell. Mar. 20, 2012; 21(3): 418-429. (Year: 2012).*

Peduto et al. ADAM12 is highly expressed in carcinoma-associated stroma and is required for mouse prostate tumor progression. Oncogene (2006) 25, 5462-5466. (Year: 2006).*

Scott et al. Antibody therapy of cancer. Nature, 12, 2012, 278-287. (Year: 2012).*

Kodama et al. ADAM12 Is Selectively Overexpressed in Human Glioblastomas and Is Associated with Glioblastoma Cell Proliferation and Shedding of Heparin-Binding Epidermal Growth Factor. Am J Pathol . Nov. 2004;165(5):1743-53. (Year: 2004).*

Vlad et al. Expression of CDCP1 and ADAM12 in the ovarian cancer microenvironment. JBUON 2016; 21(4): 973-978. (Year: 2016).*

Frohlich et al. Molecular Profiling of ADAM12 in Human Bladder Cancer. Clin Cancer Res 2006; 12(24) Dec. 15, 2006. (Year: 2006).*

Liu et al., Fibroblast activation protein: A potential therapetuic target in cancer. Cancer Biology & Therapy, 2012, 13, 123-129. (Year: 2012).*

Jia et al. GPR30 Promotes Prostate Stromal Cell Activation via Suppression of ERα Expression and Its Downstream Signaling Pathway. Endocrinology. Aug. 2016;157(8):3023-35. (Year: 2016).*

Duvillard Christian et al., "EDTA enhances the anti tumor efficacy of intratumoral cisplatin in s. c. grafted rat colon tumors", XP002769069, Database accession No. PREV200400263801 Database BIOS IS [Online] Biosciences Information Service, Philadelphia, PA, US; Mar. 2004 (Mar. 2004).

L Peduto et al: "ADAM12 is highly expressed in carcinoma-associated stroma and is required for mouse prostate tumor progression", ONCOGENE, vol. 25, No. 39, Aug. 31, 2006 (Aug. 31, 2006), pp. 5462-5466, XP055118927, ISSN: 0950-9232, DOI: 10.1038/sj.onc.1209536.

Naoko Yamane-Ohnuki et al: "Production of therapeutic antibodies with controlled fucosylation", MABS, Landes Bioscience, US, vol. 1, No. 3, May 1, 2009 (May 1, 2009), pp. 230-236, XP002731447, ISSN: 1942-0862. DOI: 10.4161/MABS.1.3.8328.

R. Albrechtsen et al: "ADAM12 redistributes and activates MMP-14, resulting in gelatin degradation, reduced apoptosis and increased tumor growth", Journal of Cell Science,vol. 126, No. 20,Sep. 4, 2013 (Sep. 4, 2013), pp. 4707-4720, XP055157165,ISSN: 0021-9533, DOI: 10.1242/jcs.129510.

M. Kveiborg et al: "A Role for ADAM12 in Breast Tumor Progression and Stromal Cell Apoptosis",Cancer Research,vol. 65, No. 11, Jun. 1, 2005 (Jun. 1, 2005), pp. 4754-4761, XP055363283, us ISSN: 0008-5472, DOI: 10.1158/0008-5472.CAN-05-0262.

Roy R et al: "ADAM 12 cleaves extracellular matrix proteins and correlates with cancer status and stage", Journal of Biological Chemistry, American Society for Biochemistry and Molecular Biology, US, vol. 279, No. 49, Dec. 3, 2004 (Dec. 3, 2004), pp. 51323-51330, XP002321631, ISSN: 0021-9258, DOI: ISSN: 0021-9258, DOI: 10.1074/JBC.M409565200.

* cited by examiner

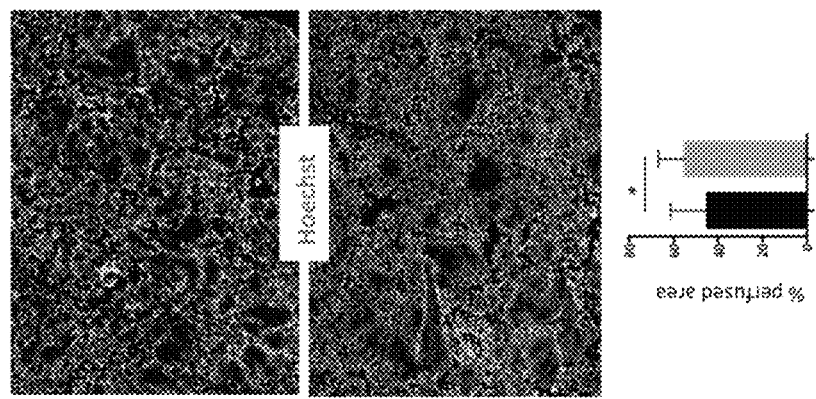
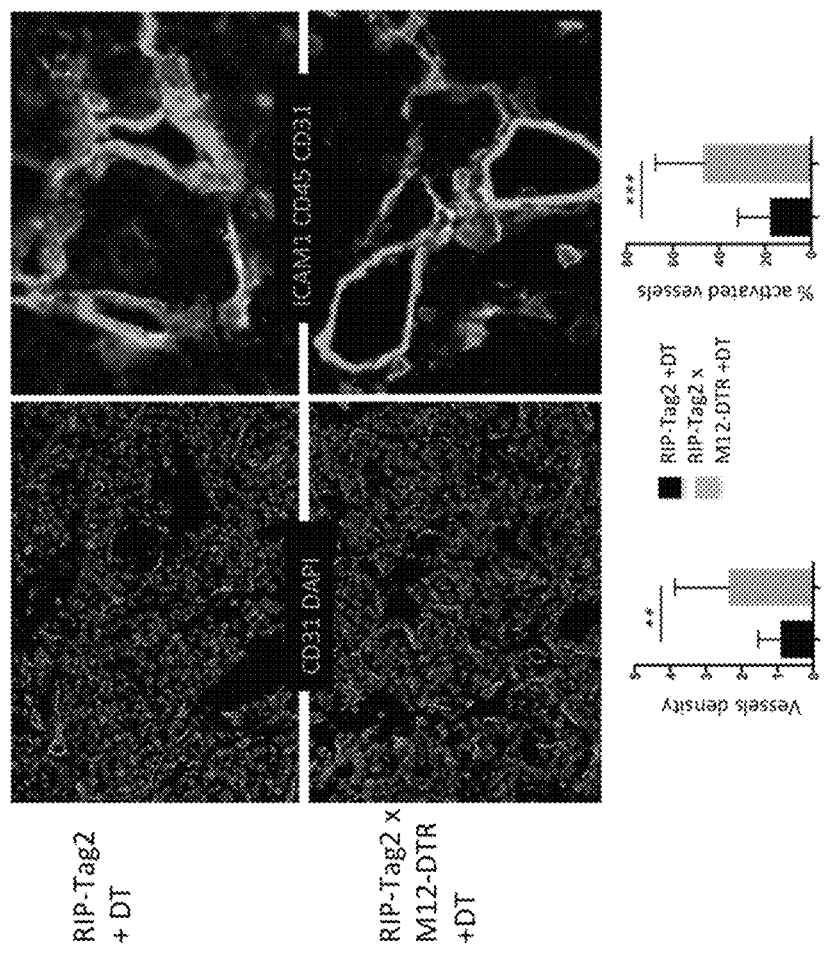

USE OF INHIBITORS OF ADAM12 AS ADJUVANTS IN TUMOR THERAPIES

CROSS REFERENCE TO RELATED APPLICATIONS

This application is a national stage application under 35 U.S.C. § 371 of International Application No. PCT/EP2017/052453, filed on Feb. 3, 2017, that designates the United States and claims the benefit under 35 U.S.C. § 119(e) of U.S. provisional patent application No. 62/291,656, filed Feb. 5, 2016, all of which are incorporated herein by reference in their entirety

FIELD OF THE INVENTION

The present invention relates to the field of tumors and more particularly to the use of ADAM12 (a Disintegrin and Metalloproteinase 12) inhibitors as adjuvant therapy in combination with current anti-tumor therapies for the treatment of solid tumors including melanoma.

BACKGROUND

Standard therapies for solid tumors include one or more cycles of treatment with different cytotoxic, anti-angiogenic or targeted therapies, depending on the tumor type/stage. Even though the treatment of choice might be initially beneficial, relapses are common and reflect development of acquired resistance. These relapses, which often correlate with high tumor burden, are the main cause of treatment failure and mortality related to cancer. As a matter of fact, large tumors have usually a poorly functional and abnormal vasculature and high stromal content, resulting in a poor perfusion and compromised access for drugs and immune cells to the central regions of the tumor. Altogether, this creates an immunosuppressive and pro-tumorigenic environment.

To increase chances to limit tumor resistance, it is beneficial to co-target both tumor cells and its stromal microenvironment. Current evidence indicate that mesenchymal stromal cells developing in tumors (also called carcinoma-associated fibroblasts—CAFs) play an essential role in creating an immunosuppressive and pro-tumorigenic environment, altogether favoring drug resistance. Only a few markers are currently available to target CAFs, such as Fibroblast Activation Protein (FAP) and Platelet-Derived Growth Factor Receptor alpha (PDGFR alpha), however these proteins are also expressed in fibroblasts in healthy organs, which is a major limitation for a therapeutic use. A membrane-bound protease called ADAM12 (A Disintegrin And Metalloprotease 12) has previously been identified as being highly expressed in a specific subset of CAFs participating in tumor-stroma crosstalk in prostate, breast, and colon cancer (Peduto, L., et al., *Oncogene* 25, 5462-5466 (2006)).

ADAM12 is transiently expressed during development and is downregulated in adult organs at homeostasis. ADAM12 is re-expressed in fibrotic diseases and desmoplastic tumors, including tumors of the prostate, breast, colon, bladder, lung, pancreas, liver, gastric tumors and fibromatosis (Peduto, L., et al., *Oncogene* 25, 5462-5466 (2006); Le Pabic, H., et al., *Hepatology* 37, 1056-1066. (2003); Borneman et al., *J. Muscle Res. Cell. Motil.* 21, 475-480. (2000); Shi-Wen, X., et al., *Matrix Biol.* 26, 625-632. (2007); Narita, D., et al., *Acta Histochem.* 114, 131-139. (2012); Carl-McGrath, S., et al., *Int J Oncol.* 26, 17-24. (2005); Frohlich, C., et al., *Clin Cancer Res.* 12, 7359-7368. (2006); Mino, N., et al., *J Surg Oncol.* 100, 267-272. (2009); Bourd-Boittin, K. et al., Contribution to liver fibrogenesis. *J Biol Chem* 283, 26000-26009 (2008)). As it is poorly expressed in normal organs, ADAM12 might represent an interesting therapeutic target for clinical use.

ADAMs are a family of cell surface metallopeptidases that have key roles in cell-cell interactions because of their ability to cleave and release growth factors, cytokines, receptors, adhesion molecules and other molecules from the plasma membrane. This process, which is referred to as protein ectodomain shedding of membrane-anchored molecules has merged as an important posttranslational regulator of the function of many cleaved substrate proteins, including EGF-receptor ligands and TNFα. More than 30 members have been identified in the ADAM family with a broad tissue distribution and have been involved in several cellular processes. Due to their ability to rapidly affect key signalling activities between cells and their environment, ADAM family members could conceivably contribute to tumorigenesis, especially if their function is dysregulated. Therefore, they are making up the majority of pharmaceutical targets currently undergoing preclinical and clinical evaluation (Moss et al., "ADAMs: Targets for Drug Discovery" Current Pharmaceutical Design, June 2009).

ADAM12 is known to be an active protease involved in the activation of several growth factors pathways, including the Epidermal Growth Factor Receptor (EGFR), and plays a role in tumor progression by modulating tumor-stroma crosstalk (Peduto et al., Oncogene, 2006, 25, 5462-5466). In addition to cancer, ADAM12 is also involved in chronic diseases such as fibrotic diseases, arthritis, cardiac hypertrophy and neurodegenerative diseases (Jacobsen & Wewer, Current Pharmaceutical Design, 2009, 15, 2300-2310).

There is a need in the art for additional treatments for cancer. The invention fulfills this need in the art.

SUMMARY OF THE INVENTION

The invention encompasses compositions or kits of parts for administration to a cancer patient. The invention further encompasses methods for enhancing anti-tumor immune responses in a patient.

In various embodiments, the composition or kit of parts comprises an ADAM12 inhibitor and an anti-tumor compound.

In various embodiments, the method comprises administering to the patient a combination of an ADAM12 inhibitor and an anti-tumor compound.

In various embodiments, the ADAM12 inhibitor is an immunoconjugate that comprises a monoclonal antibody or antibody fragment that binds ADAM12 protein on the surface of cells.

In various embodiments, the anti-tumor compound is selected from the group consisting of: a Tumor-Specific Antigen (TSA), a Tumor-Associated Antigen (TAA), an antibody, a modified immune cell, a cytokine, an immune checkpoint blockade molecule, a virus or nucleic acid vector, a chemotherapy drug, and an anti-angiogenic drug.

In various embodiments, the Tumor-Specific Antigen (TSA) or Tumor-Associated Antigen (TAA) is selected from MAG-Tn3 (Multiple Antigen Glycopeptide-T-nouvelle (CD175)3 as disclosed in EP 2 500 033), Melanoma Associated Antigen-A3 (MAGE-A3), New York esophageal squamous cell carcinoma antigen (NY-ESO-1), Human Epidermal Growth Factor Receptor 2 (HER-2/neu), Cellular tumor antigen p53 (p53), melanoma-associated antigen recognized by T cells 1 (MART-1), Melanocyte protein PMEL (glycoprotein (gp) 100), Alphafetoprotein (AFP), Epidermal Growth Factor Receptor Variant III (EGFRvIII)-specific 14-amino acid peptide, PEP-3 chemically conjugated to keyhole limpet hemocyanin (KLH), Mucin-16 (CA-125), Mucin-1 (MUC-1), carcinoembryonic antigen (CEA), Epithelial tumor antigen (ETA), Tyrosinase, prostatic acid phosphatase (PAP), prostate-specific antigen (PSA), Sialyl-Tn antigen (CD175s), prostate specific membrane antigen (PSMA), and non-catalytic human telomerase reverse transcriptase (hTERT).

In various embodiments, the antibody is a monoclonal antibody that targets CD52, Epidermal Growth Factor Receptor (EGFR), VEGF (Vascular Endothelial Cell Receptor), Human Epidermal Growth Factor Receptor 2 (HER-2), CD20, CD16, CD134 (OX40), CD137, CD27, Tumor necrosis factor receptor superfamily member 18 (GITR or CD357), CD40, CD19, CD272, CD279, CD274, PAP, CD38, CD47, or disialoganglioside (GD2).

In various embodiments, the modified immune cell is a dendritic cell.

In various embodiments, the dendritic cell expresses a PAP antigen.

In various embodiments, the modified immune cell is a T cell.

In various embodiments, the modified immune cell expresses a chimeric antigen receptor (CAR). In various embodiments, the CAR is directed against CD19, melanoma-associated antigen recognized by T cells 1 (MART-1), glycoprotein (gp) 100, carcinoembryonic antigen (CEA), p53, MAGE-A3, or New York esophageal squamous cell carcinoma antigen (NY-ESO-1).

In various embodiments, the cytokine is an interferon or an interleukin.

In various embodiments, the immune checkpoint blockade molecule is a monoclonal antibody that targets Cytotoxic T-lymphocyte associated protein 4 (CTLA-4 or CD152), Programmed Death-Ligand 1 (PD-L1, CD274 or B7H1) or Programmed cell Death protein 1 (PD-1 or CD279).

In various embodiments, the virus expresses a 5T4 tumor-associated antigen (Trophoblast glycoprotein or 5T4 oncofetal antigen).

In various embodiments, the method, composition or kit of parts further comprises an adjuvant or immune modulator selected from Granulocyte-Macrophage Colony-Stimulating Factor (GM-CSF), Keyhole Limpet Hemocyanin (KLH), liposomal AS15 (QS-21, Monophosphoryl lipid-A (MPL), CpG oligodeoxynucleotide), BCG (Bacillus Calmette-Guérin), freeze dried BCG, MONTANIDE™, Interleukin 2 (IL-2), and KLH.

In various embodiments, the ADAM12 inhibitor is a monoclonal antibody having ADCC activity or CDC activity and that binds ADAM12 on the surface of cells. Preferably, the monoclonal antibody has a low fucose content.

In various embodiments, the method, composition or kit of parts further comprises a Dipeptidylpeptidase 4 (DPP4) inhibitor selected from Sitagliptin, Vildagliptin, Saxagliptin, Linagliptin, Anagliptin, Teneligliptin, Alogliptin, Gemigliptin and Dutogliptin.

The invention encompasses an ADAM12 inhibitor for depleting stromal cells encapsulating solid cancer cells, wherein the ADAM12 inhibitor is a monoclonal antibody with ADCC activity or CDC activity directed against the ADAM12 protein on the surface of the stromal cells. Preferably, the monoclonal antibody has a low fucose content.

DETAILED DESCRIPTION OF THE INVENTION

Tumor therapies often fail, or become inefficient after some time, because drugs and tumor specific T cells cannot access anymore the core of the tumor. This happens because tumor growth induces structural changes in the tumor microenvironment leading to hypoxia (lack of vessels) in the center of the tumor whereas functional vasculature and infiltrating immune cells targeting the tumor cells remain trapped in the tumor margins, also called the tumor stromal capsule because composed of a subpopulation of stromal cells adjacent to tumor cells. This is characteristic of most carcinomas, including melanoma, breast, colon, bladder, prostate, pancreatic, liver and lung tumors.

The present inventors have unexpectedly found that it is advantageous to deplete cells expressing ADAM12 protein as an adjuvant therapy for the treatment of cancer. ADAM12+ stromal cells produce extracellular matrix such as collagen, angiogenic factors and chemokines, which attract T cells and other immune cells. Disrupting the stromal capsule restores a better vasculature/tumor perfusion and improve T cells infiltration inside the core of a melanoma.

Figure 1A:
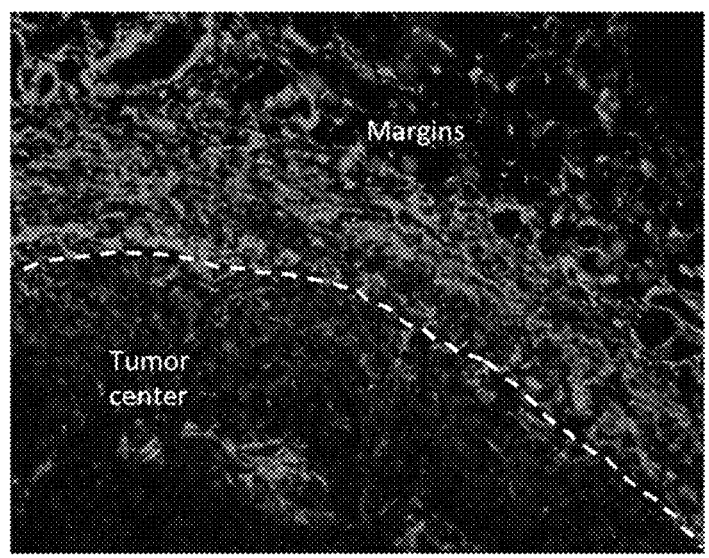
FIG. 1A-B: (A) ADAM12+ carcinoma-associated fibroblasts (CAFs) develop in the gp38+ tumor stroma at the tumor margins in a murine melanoma model. (B) ADAM12+ CAFs isolated by FACS from the tumor express all PDGFRα (right panel). On the left panel, stroma isolated from melanoma in control GFP− mice do not have GFP signal.
Figure 1B:
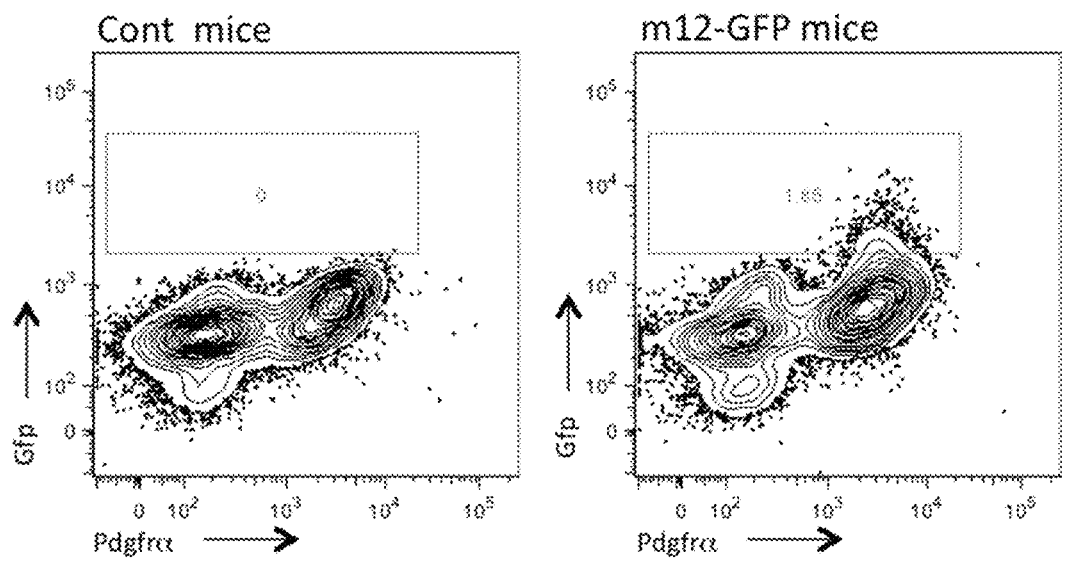

A mouse system was engineered that expresses the diphtheria toxin receptor in ADAM12+ cells. In this system, injection of diphtheria toxin in mice induces specific depletion of ADAM12+ cells. Using this system, the growth of a melanoma can be significantly reduced by depleting ADAM12+ stromal cells. After this treatment, tumors are better perfused and are infiltrated with T cells inside the core of the tumor (i.e., the central region of the tumor or tumor center), which are now able to kill the tumor cells The development of ADAM12+ cells was seen in the tumor stroma at the peripheral margins of the tumor in ADAM12-GFP mice injected with melanoma cells (FIG. 1A). The ADAM12+ cells were identified as PDGFRα+ carcinoma-associated fibroblasts (CAFs) (FIG. 1B)

Figure 2:
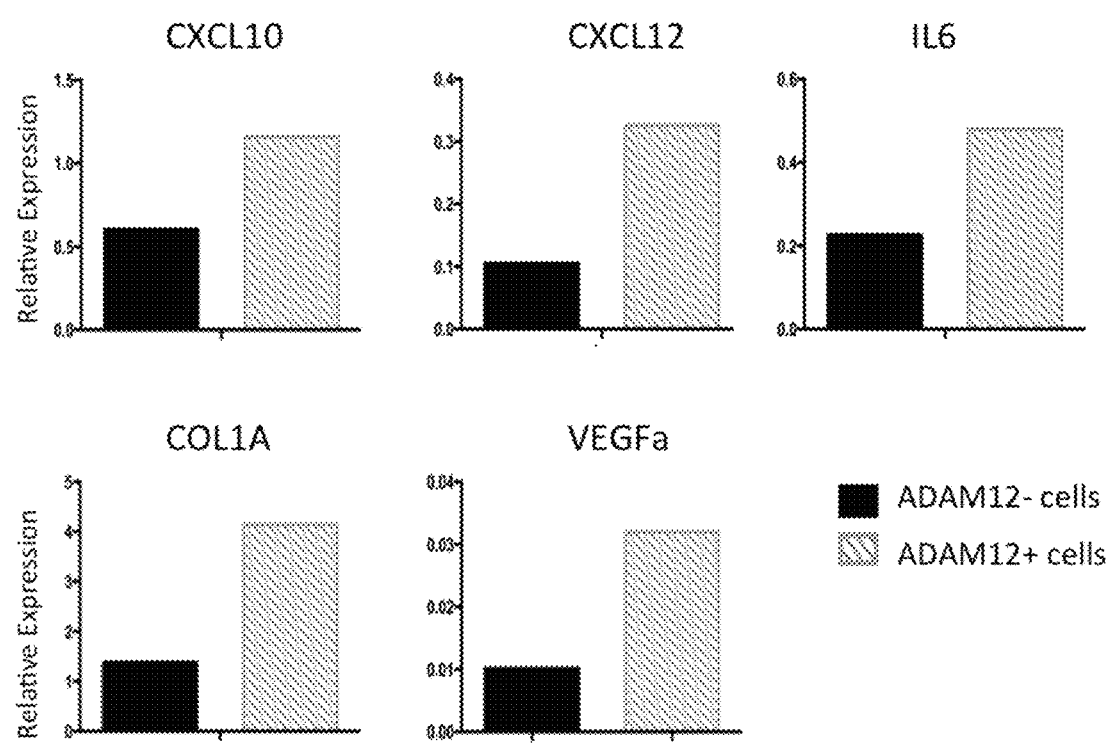
FIG. 2: Gene expression of ADAM12+ and ADAM12− stromal cells isolated from melanoma tumors.

Total RNA was extracted from ADAM12+ and ADAM12– CAFs from melanoma, and transcripts expression was analyzed. ADAM12+ CAFs expressed higher levels of transcripts for the chemokines CXCL10 and CXCL12, as well as the pro-inflammatory cytokine IL6, as compared to ADAM12– CAFs. In addition, ADAM12+ CAFs expressed high levels of the pro-angiogenic factor VEGFa, as well as transcript coding for type I collagen (FIG. 2). These results show that ADAM12+ CAFs are an immunomodulatory and proangiogenic subset of CAFs.

Figure 3B:
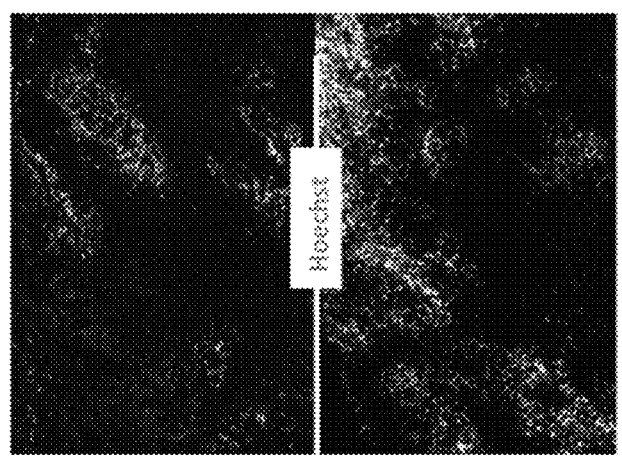
FIG. 3A-B-C-D: Tumors lacking ADAM12+ stromal cells have increased CD31+ vessel density, increased vessels activation (ICAM+) (A and C) and better perfusion (B and D). A and B: melanoma mice model. C and D: RIP-Tag2 neuroendocrine pancreatic tumor mice model. DAPI stains the cell nuclei. "Cont" means control mice that refers to non-transgenic mice (DTR negative).
Figure 3B:
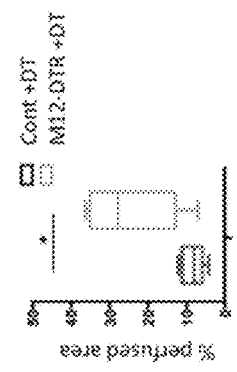
Figure 3A:
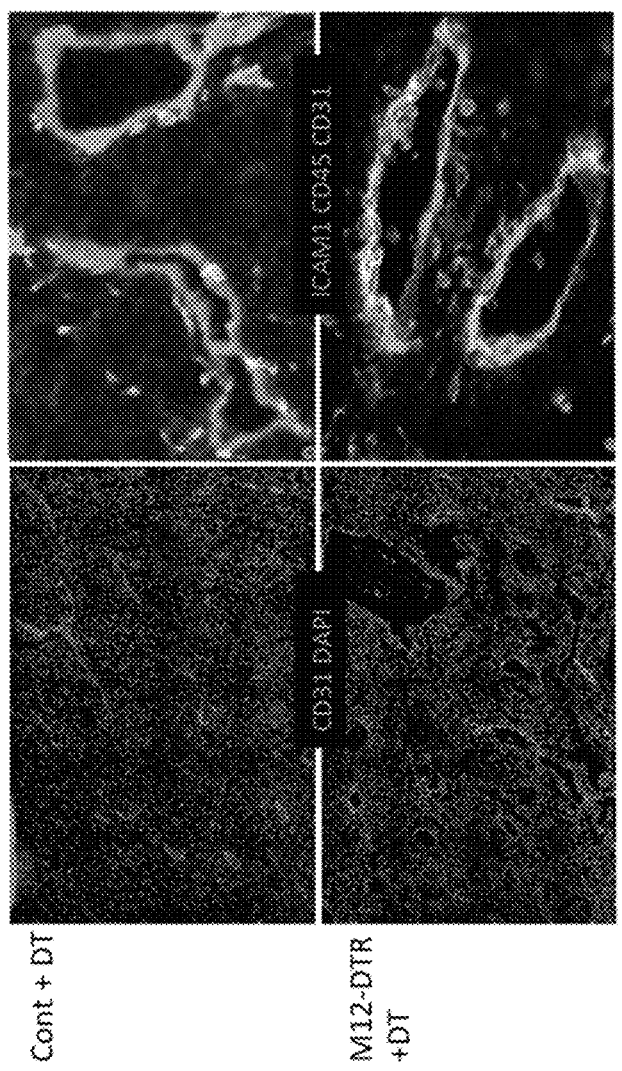
Figure 3A:

Melanoma cells were injected into mice, and the mice were specifically depleted for ADAM12+ CAFs starting when tumors were palpable at day 9 or 10. Two or three weeks after tumor inoculation, melanoma tumors were isolated. Tumors lacking ADAM12+ CAFs had a higher density of CD31+ vessels inside the tumors. In addition, CD31+ vessels displayed an activated ICAM1+ phenotype (FIG. 3A). In addition, tumors lacking ADAM12+ CAFs had increased perfusion (FIG. 3B).

Figure 4A:
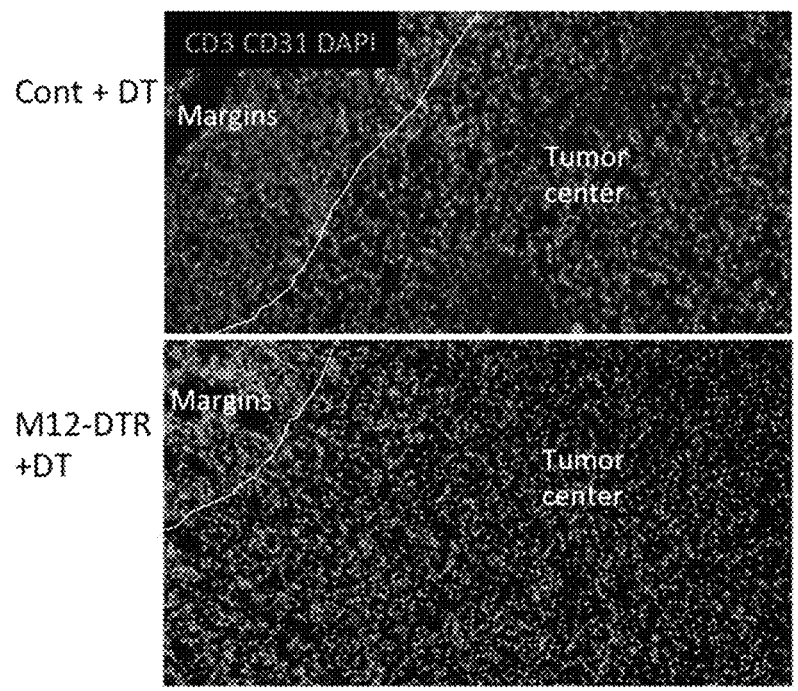
FIG. 4A-B: In melanoma mice model tumors lacking ADAM12+ stromal cells (in M12-DTR mice injected with DT-diphtheria toxin) have higher T cells (CD3+) infiltration inside the tumor (A), leading to a decrease in tumor growth (B). Both "Cont" and "Ctrl" mean control mice that refers to non-transgenic mice (DTR negative).
Figure 4A:
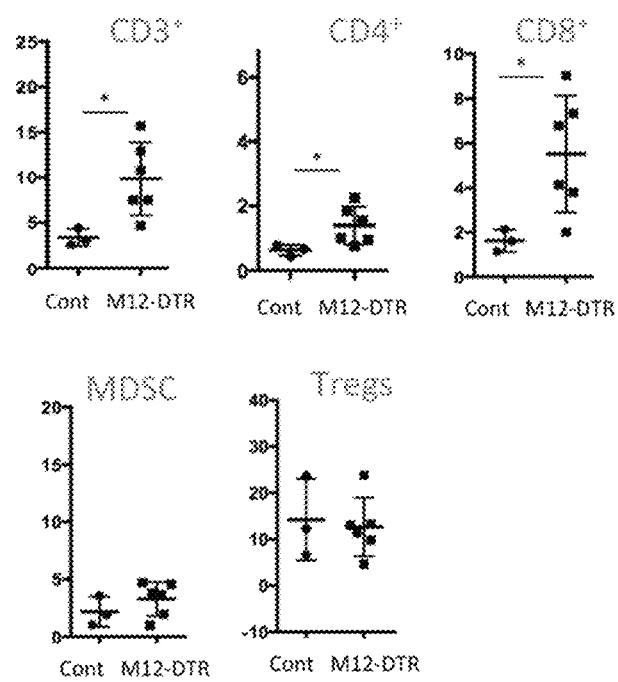
Figure 4B:
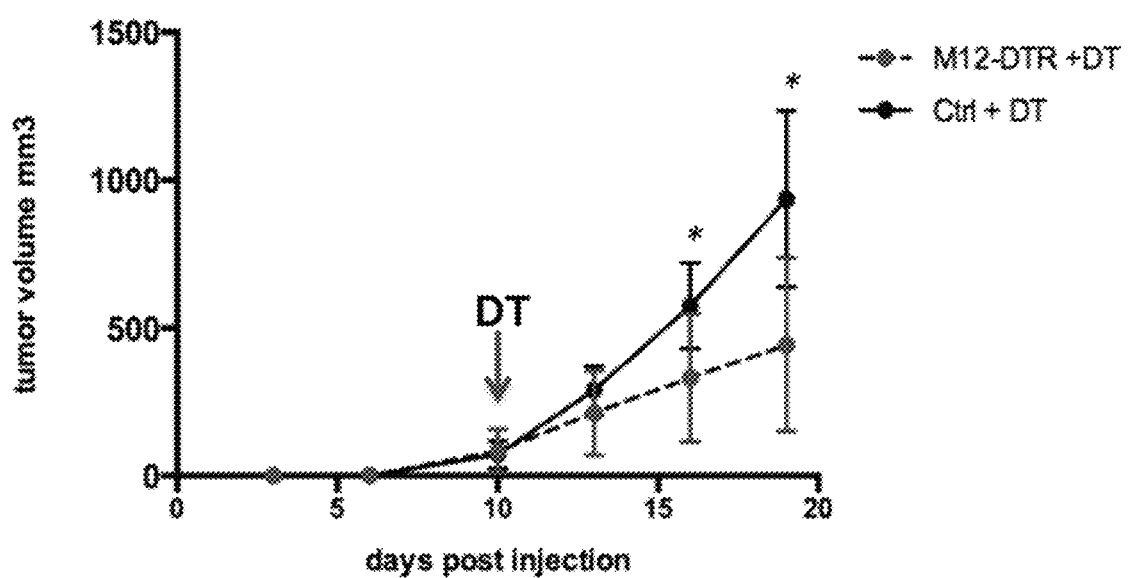

Depletion of ADAM12+ CAFs improves T cells infiltration inside the tumor, and limits tumor growth. Tumors lacking ADAM12+ CAFs displayed significantly higher frequency of CD3+ T cells compared to tumors with normal stroma (FIG. 4A, right panel). This effect was specific for T cells, as other immune populations remained unchanged (such as myeloid-derived suppressor cells—MDSC) and T regulator cells—Tregs). The ratio of M1/M2 macrophages was also increased, favoring anti-tumoral M1 macrophages. In addition, CD3+ T cells were now recruited to the core of the tumor, in contrast to tumors harboring a normal tumor stroma (FIG. 4A, left panel). Thus, tumor growth can be significantly delayed when ADAM12+ CAFs are depleted (FIG. 4B).

The invention encompasses methods, compositions, and kits for the depletion of ADAM12+ CAFs in cancer patients.

ADAM12 Inhibitors and Uses thereof

Accordingly, it is an object of the invention to use compounds or agents that specifically deplete ADAM12+ cells. As used herein, the term "deplete" when referring to ADAM12+ cells refers to the killing of ADAM12+ cells or reducing the biological activity of the cells that express ADAM12 protein. An ADAM12 inhibitor contemplated by the present invention has the ability to interact specifically with ADAM12+ cells in such a way as to specifically deplete the ADAM12+ cells or stop their proliferation or reduce the biological activity of cells that express ADAM12 protein. Thus, within the context of the invention, an "ADAM12 inhibitor" is a compound that kills or prevents the proliferation of ADAM12+ cells or reduces the biological activity of cells that express ADAM12 protein, but which does not substantially kill or prevent the proliferation of other cells that do not express ADAM12 protein. With respect to the contemplated molecules used in accordance with the present invention, the expression "specifically deplete" refers to a compound or agent that specifically recognizes ADAM12 protein on the cell surface and reduces the level or activity of the cells expressing ADAM12 protein, but which does not reduce the level or activity of other cells that do not express ADAM12 protein. Preferably, the ADAM12 inhibitor is a compound that specifically kills ADAM12+ cells, but does not substantially kill other cells that do not express ADAM12 protein.

According to the invention, the ADAM12 inhibitors are used to disrupt the tumor stromal capsule for improving the vasculature, tumor perfusion and T cells infiltration in the central region of the tumor, and for limiting macrophage polarization toward an immunosuppressive M2 phenotype.

Molecules that deplete or neutralize the activity of ADAM12+ cells include compounds or agents, including monoclonal antibodies and antibody fragments, that bind to ADAM12 protein on the cell surface and induce cell damage, either by neutralizing the biological activity of ADAM12, or by direct toxic effect such as when linked to a toxic molecule (e.g. immunoconjugates), or by antibody-dependent cellular cytotoxicity (ADCC activity), or by cytotoxicity induced by the complement (CDC activity).

Molecules which neutralize the biological activity of ADAM12 protein include compounds or agents that neutralize its proteolytic activity, its adhesion activity and/or its cytoplasmic signal transduction activity.

As one skilled in the art will appreciate, inhibitors contemplated by the present invention may be but are not limited to, an antibody, a small organic molecule, an enzyme, a peptide, or a hormone.

More particularly, the inhibitory compounds may be those that are known to affect ADAM12 proteolytic activity including: hydroxamate inhibitors, thiol amides which exhibit collagenase inhibition activity (U.S. Pat. No. 4,595,700), N-carboxyalkyl derivatives containing a biphenylethylglycine which inhibit MMP-3, MMP-2 and collagenase (Durette, et al., WO 95/29689), lactam derivatives which inhibit matrix metalloproteases, TNF-alpha and aggrecanase (see U.S. Pat. No. 6,495,699), tricyclic sulfonamide compounds (see U.S. Pat. No. 6,492,422), the compound ONO-4817 (Ono Pharmaceutical Co. Ltd., Osaka, Japan; see also Mori, et al., 2002, Anticancer Res., 22(6C):3985-8) and the collagenase inhibitors GM6001 (trade name Galardin) and GM1489 (a derivative of GM6001) (see U.S. Pat. No. 6,759,432). Specific examples of hydroxamic acid-based metalloprotease inhibitors include the compounds "5A" [NHOHCOCH2CH(i-Bu)CO-tryptophan-NHMe], "21A" [NHOHCOCH2CH(i-Bu)CO-tryptophan-NHCHMePh], "39A" [HOOCCH2CH(i-Bu)CO-tryptophan-NHCHMePh], "S1209" [NHOHCOCH2CH(i-Bu)CO-tyrosine-OMeNHMe], UL001 [HSCH2 CH(CH2CH(CH3)2)CO-Phe-Ala-NH2] and MP506 (Elastin Products Company, Inc.) (See U.S. Pat. Nos. 5,773,438 and 5,892,112). Other compounds, such as KB-R7785, could act as inhibitors of ADAM12 (Oh et al., 2004, Bioorg Med Chem. Lett., 14(24): 6071-6074). The matrix metalloprotease inhibitor SB-3CT is also expected to inhibit ADAM12. Additional metalloprotease inhibitors expected to be useful as ADAM12 inhibitory compounds include the various compounds disclosed in U.S. Pat. Nos. 6,500,847; 6,268,379; 5,968,795; 5,892,112; 5,872,152; 4,681,894; 4,943,587 and WO 06/014903. Four selective ADAM12 inhibitors have been described by Myungsok et al, 2004 ("Structure-based virtual screening and biological evaluation of potent and selective ADAM12 inhibitors"), called the compounds 5, 11, 14, and 16.

The invention encompasses methods, compositions, and kits of parts comprising an ADAM12 inhibitor and the anti-tumor compound.

Compositions and Kits of Parts

The invention encompasses a composition or kit of parts for administration to a cancer patient comprising an ADAM12 inhibitor and an anti-tumor compound.

The composition or kit of parts may be in a single vial or container or may be in multiple vials or containers.

The composition or kit of parts is for simultaneous or sequential administration to the patient. The administration can be by conventional means including intravenous, oral, intramuscular, intratumoral, subcutaneous, and intranasal administration. A different form of administration may be used for the ADAM12 inhibitor and the anti-tumor compound.

Simultaneous administration of the ADAM12 inhibitor and the anti-tumor compound can be at the same time or within 1, 2, 3, or 4 hours of each other.

Sequential administration of the ADAM12 inhibitor and the anti-tumor compound can be in either order and after 4 hr, 8 hr, 12 hr, 24 hr, 2 days, 3 days, 4 days, 1 week, 2 weeks, etc, of each other.

Anti-tumor therapies that might benefit from adjuvant therapy with an ADAM12 inhibitor include, but are not limited to: chemotherapies, immunotherapies, tumor targeting monoclonal antibodies, and anti-angiogenic drugs, or a combination of these drugs.

In some embodiments, the anti-tumor compound is selected from a Tumor-Specific Antigen (TSA), a Tumor-Associated Antigen (TAA), an immune adjuvant or an immune modulator, an antibody or antibody fragment, a modified immune cell, a cytokine, an immune checkpoint blockade molecule, a virus, an anti-angiogenic compound, and a chemotherapy compound.

According to the invention, the ADAM12 inhibitor of the composition or kits of parts is used to disrupt the tumor stromal capsule for improving the vasculature, tumor perfusion and T cells infiltration in the central region of the tumor and for limiting macrophage polarization toward an immunosuppressive M2 phenotype.

Anti-ADAM12 Antibodies

The invention encompasses isolated antibodies and antibody fragments that bind specifically to ADAM12 protein.

In some embodiments, purified proteins are used to produce antibodies by conventional techniques. In some embodiments, recombinant or synthetic proteins or peptides are used to produce antibodies by conventional techniques.

Antibodies can be synthetic, semi-synthetic, monoclonal, or polyclonal and can be made by techniques well known in the art. Such antibodies specifically bind to proteins and polypeptides via the antigen-binding sites of the antibody (as opposed to non-specific binding). Purified or synthetic proteins and peptides can be employed as immunogens in producing antibodies immunoreactive therewith. The proteins and peptides contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art. Such epitopes or variants thereof can be produced using techniques well known in the art such as solid-phase synthesis, chemical or enzymatic cleavage of a polypeptide, or using recombinant DNA technology.

Antibodies are defined to be specifically binding if they bind proteins or polypeptides with a Ka of greater than or equal to about $10^7$ $M^{-1}$. Affinities of binding partners or antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, goats, sheep, dogs, chickens, rabbits, mice, or rats, using procedures that are well known in the art. In general, a purified protein or polypeptide that is appropriately conjugated is administered to the host animal typically through parenteral injection. The immunogenicity can be enhanced through the use of an adjuvant, for example, Freund's complete or incomplete adjuvant. Following booster immunizations, small samples of serum are collected and tested for reactivity to proteins or polypeptides. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543, 439, and 4,411,993; Monoclonal Antibodies, Hybridomas: A New Dimension in Biological Analyses, Plenum Press, Kennett, McKeam, and Bechtol (eds.), 1980.

For example, the host animals, such as mice, can be injected intraperitoneally at least once and preferably at least twice at about 3 week intervals with isolated and purified proteins or conjugated polypeptides, for example a peptide comprising or consisting of the specific amino acids set forth above. Mouse sera are then assayed by conventional dot blot technique or antibody capture (ABC) to determine which animal is best to fuse. Approximately two to three weeks later, the mice are given an intravenous boost of the protein or polypeptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled protein or polypeptide, is added to each well followed by incubation. Positive wells can be subsequently detected. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", Strategies in Molecular Biology 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies can be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment can comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, May, 1993). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol. 139:3521 3526, 1987; Sun et al. PNAS 84:214 218, 1987; Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229: 1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol. 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

In one embodiment, the invention encompasses single-domain antibodies (sdAb), also known as NANOBODIES. A sdAb is a fragment consisting of a single monomeric variable antibody domain that can bind selectively to a specific antigen.

In one embodiment, the sdAbs are from heavy-chain antibodies found in camelids (VHH fragments), or cartilaginous fishes (VNAR fragments), or are obtained by splitting dimeric variable domains into monomers.

In one embodiment, the anti-ADAM12 antibodies are monoclonal antibodies having high ADCC (Antibody-Dependent Cell-Mediated Cytotoxicity) or high CDC (Complement Dependent Cytotoxicity).

In a preferred embodiment the monoclonal antibodies having high ADCC activity have a low fucose content. Low fucose content refers to antibodies which possess on the glycosylation site of their Fc region (position 297) an oligosaccharide having low fucose levels. Such antibodies with a low fucose content can be obtained by using, for example, methods described in WO2005040221, WO2006133148, WO2009135181, and WO201212500, which are hereby incorporated by reference.

Immunoconjugates

In a preferred embodiment, the ADAM12 inhibitor is an immunoconjugate comprising an antibody or antibody fragment that binds to ADAM12 protein on the surface of cells. Preferably, the immunoconjugate comprises a monoclonal antibody or fragment thereof that recognizes ADAM12 protein on the surface of cells.

Preferably, the immunoconjugate further comprises a toxin that is either cytotoxic, cytostatic, or otherwise prevents or reduces the ability of the ADAM12+ cells to divide. Thus, in one embodiment, the ADAM12 inhibitor is an immunoconjugate comprising (1) an antibody or antibody fragment that binds to ADAM12 protein on the surface of cells attached to (2) a toxin. The antibody or antibody fragment and toxin can be attached to create the immunoconjugate (i.e., immunotoxin) by creating a fusion protein or by linking the two molecules together chemically. Preferably, the immunoconjugate is internalized by the ADAM12+ cells.

In regard to the toxin components of the immunoconjugate, it is contemplated that any one of a variety of toxins may be employed. Included in the term "toxin" are the commonly designated toxins such as poisonous lectins, ricin, abrin, modeccin, botulina and diphtheria toxins, as well as other toxic agents such as radio-isotopes, cytotoxic and cytostatic drugs. Of course, combinations of the various toxins could also be coupled to one antibody molecule.

In one embodiment, the immunoconjugate comprises a toxin that blocks the protein synthesis of the ADAM12+ cell, therein leading to cell death. In preferred embodiments, the toxin comprises a polypeptide having ribosome-inactivating activity. Preferably, the toxin is selected from gelonin, bouganin, saporin, ricin, ricin A chain, bryodin, diphtheria toxin, diphtheria A chain, restrictocin, *Pseudomonas* exotoxin A chain, abrin A chain, modeccin A chain, alpha-sarcin, Aleurites fordii proteins, dianthin proteins, *Phytolacca americana* proteins (PAPI, PAPII, and PAP-S), *Momordica charantia* inhibitor, curcin, crotin, *Saponaria officinalis* inhibitor, mitogellin, phenomycin, enomycin, and variants thereof.

In preferred embodiments, the toxin moiety is a ranpirnase (Rap), such as Rap(Q). In more preferred embodiments, the immunotoxin is made using dock-and-lock (DNL) technology, for example, as described U.S. Pat. No. 8,551,480.

Conjugates of the monoclonal antibody and such cytotoxic moieties may be made using a variety of bifunctional protein coupling agents. Examples of such reagents are N-succinimidyl-3-(2-pyridyldithio) propionate (SPDP), iminothiolane (IT), bifunctional derivatives of imidoesters such as dimethyl adipimidate HCl, active esters such as disuccinimidyl suberate, aldehydes such as glutaraldehyde, bis-azido compounds such as bis(p-diazoniumbenzoyl)-ethylenediamine, diisocyanates such as tolylene 2,6-diisocyante, and bis-active fluorine compounds such as 1,5-difluoro-2, 4-dinitrobenzene.

The invention includes an immunoconjugate comprising a protein encoded by nucleic acid fusion of an antibody encoding sequence to a toxin encoding sequence.

In some embodiments, the immunoconjugate comprises an agent that acts to disrupt DNA. Preferably, the immunoconjugate comprises enediyne (e.g., calicheamicin and esperamicin) or non-enediyne small molecule agents (e.g., bleomycin, methidiumpropyl-EDTA-Fe(II)), daunorubicin, doxorubicin, distamycin A, cisplatin, mitomycin C, ecteinascidins, duocarmycin/CC-1065, or bleomycin/pepleomycin.

In some embodiments, the immunoconjugate comprises an agent that acts to disrupt tubulin. Preferably, the immunoconjugate comprises rhizoxin/maytansine, paclitaxel, vincristine and vinblastine, colchicine, auristatin dolastatin 10 MMAE, or peloruside A.

In some embodiments, the immunoconjugate comprises an alkylating agent. Preferably, the immunoconjugate comprises Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thiotepa NSC 6396, triethylenemelamine NSC 9706, uracil nitrogen mustard NSC 34462, or Yoshi-864 NSC 102627.

In some embodiments, the immunoconjugate comprises an antimitotic agent. Preferably, the immunoconjugate comprises allocolchicine NSC 406042, Halichondrin B NSC 609395, colchicine NSC 757, colchicine derivative NSC 33410, dolastatin 10 NSC 376128 (NG-auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, or vincristine sulfate NSC 67574.

In some embodiments, the immunoconjugate comprises a topoisomerase I inhibitor selected from camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In some embodiments, the immunoconjugate comprises a topoisomerase II inhibitor selected from doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In some embodiments, the immunoconjugate comprises an RNA or DNA antimetabolite selected from L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, alpha-TGDR NSC 71851, aphidicolin glycinate NSC 303812, ara-C NSC 63878, 5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

Anti-Tumor Antibodies

The invention further encompasses isolated antibodies and antibody fragments that bind specifically to TAAs, TSAs, and immune checkpoint proteins, and peptides derived therefrom as anti-tumor compounds.

Tumor targeting monoclonal antibodies include cetuximab, trastuzumab, ramucirumab, pertuzumab, panitumumab, denosumab, cetuximab In one embodiment, the anti-tumor compound comprises a monoclonal antibody that targets CD28, CD52, EGFR, VEGF, HER-2, CD20, CD16, OX40, CD137, CD27, GITR, CD40, CD19, CD272, CD279, CD274, PAP, CD38, CD47, or GD2.

In one embodiment, the anti-tumor compound comprises a monoclonal antibody that targets a transmembrane programmed cell death 1 protein (PDCD1, PD-1; also known as CD279) or its ligand, PD-1 ligand 1 (PD-L1, CD274), such as for example Nivolumab described in Pardoll, D M Nature reviews of Mar. 22, 2012, incorporated herein by reference. In one embodiment, the anti-cancer immunotherapeutic comprises a monoclonal antibody that targets B7-H3, CTLA-4 (e.g., Ipilimumab), GITR, OX40, LAG-3, CTLA-4 (CD152, or TIM-3/Tim-3L).

In one embodiment, the anti-tumor compound comprises multiple antibodies, including combinations of 2 or 3 of any of the antibodies detailed herein. In a preferred embodiment, the anti-tumor compound comprises antibodies targeting PD-1 and LAG-3.

In still another embodiment, the anti-tumor compound comprises an anti-CD47 antibody, for example as described in Keith Syson Chan et al, Proc Natl Acad Sci USA. 2009 Aug. 18; 106(33): 14016-14021, incorporated herein by reference.

In still another embodiment, the anti-tumor compound comprises an anti-GD3 or anti-GD2 antibody, for example as described in Ahmed, M; Cheung, N K (Jan. 21, 2014). "Engineering anti-GD2 monoclonal antibodies for cancer immunotherapy." FEBS Letters 588 (2): 288-97, incorporated herein by reference.

In another embodiment, the anti-tumor compound comprises Bec2, an anti-idiotypic antibody that mimics GD3, a ganglioside antigen, preferably with Bacillus Calmette-Guerin (BCG), as described in Giaccone et al., J Clin Oncol. 2005 Oct. 1; 23(28):6854-64, incorporated herein by reference.

Tumor-Specific Antigens (TSA) and Tumor-Associated Antigens (TAA)

Preferred Tumor-Specific Antigen (TSA) and Tumor-Associated Antigen (TAA) include MAG-Tn3 (See US 20140171618, incorporated herein by reference), Melanoma Associated Antigen-A3 (MAGE-A3) as described in Gaugler et al, J. Exp. Med. 179:921-930(1994) incorporated herein by reference, New York esophageal squamous cell carcinoma antigen (NY-ESO-1), HER-2/neu, p53, melanoma-associated antigen recognized by T cells 1 (MART-1), glycoprotein (gp) 100, Alphafetoprotein (AFP), EGFRvIII-specific 14-amino acid peptide PEP-3 chemically conjugated to keyhole limpet hemocyanin (KLH), CA-125, MUC-1, carcinoembryonic antigen (CEA), Epithelial tumor antigen (ETA), Tyrosinase, prostatic acid phosphatase (PAP), prostate-specific antigen (PSA), Sialyl-Tn, prostate specific membrane antigen (PSMA), and non-catalytic hTERT.

Other preferred TSA and TAA include epidermal growth factor receptor, survivin, ras, LAGE-1, MAGE-A4, SSX-2, RCAS1, and WT1. Other TSA and TAA are described in Melero, I. et al. (2014), Therapeutic vaccines for cancer: an overview of clinical trials 2014 September; 11(9):509-24, and Hong et al., World J Hepatol. 2015 Jun. 18; 7(11): 1581-1585, which are hereby incorporated herein by reference.

The TSAs and TAAs can be delivered as proteins/peptides, nucleic acids encoding these antigens, or using viral vectors.

In a preferred embodiment, the peptide vaccine is vitespen, an autologous cancer vaccine derived from tumor-specific gp96 heat shock proteins.

Many tumors express mutations. These mutations potentially create new targetable antigens (neoantigens) for use in immunotherapy.

Immune Adjuvants and Immune Modulators

Preferred immune adjuvants/immune modulators include TLR agonists, preferably TLR9 agonists, for example CpG and PF-3512676. See, e.g., Pashenkov, M., et al., *J Clin Oncol* 24, 5716-5724 (2006); Krieg, A. M., *Nucleic Acid Ther* 22, 77-89 (2012), which are hereby incorporated by reference.

The invention further contemplates a composition or kit of parts for immunotherapy comprising an ADAM12 inhibitor, an anti-tumor compound, preferably a Tumor-Specific Antigen (TSA) or a Tumor-Associated Antigen (TAA), and an adjuvant or immune modulator such as GM-CSF, KLH, liposomal AS15, BCG, freeze dried BCG, MONTANIDE, IL2, KLH, or Picibanil (a mixture of group A *streptococcus*).

DPP4 Inhibitors

The invention further contemplates methods, compositions, or kit of parts for administration to a cancer patient comprising a Dipeptidylpeptidase 4 (DPP4) inhibitor. In preferred embodiments, the methods, compositions, or kit of parts comprise an ADAM12 inhibitor, an anti-tumor compound, and a DPP4 inhibitor. Preferably, the DPP4 inhibitor is selected from trelagliptin, sitagliptin, vildagliptin, saxagliptin, linagliptin, anagliptin, teneligliptin, alogliptin, gemigliptin, dutogliptin, berberine, and lupeol. In some embodiments, the DPP4 inhibitor is selected from sitagliptin, vildagliptin, saxagliptin, linagliptin, anagliptin, teneligliptin, alogliptin, gemigliptin and dutogliptin. More preferably, the DPP4 inhibitor is selected from trelagliptin sitagliptin, vildagliptin, saxagliptin, alogliptin and linagliptin, most preferably selected from sitagliptin, linagliptin, and alogliptin.

Modified Immune Cells

The invention encompasses modified immune cells including dendritic cells. The immune cells can be loaded with a protein. See U.S. Pat. No. 7,414,108. The immune cells can be loaded with an RNA. See U.S. Pat. No. 7,105,157, which is hereby incorporated by reference.

The immune cell therapy can be SIPULEUCEL-T, BELAGENPUMATUCEL-L, or TERGENPUMATUCEL-L (Villaruz et al. Transl Lung Cancer Res. 2014 February; 3(1): 2-14.), incorporated herein by reference.

In a preferred embodiment, the modified immune cell is a dendritic cell that expresses a PAP antigen.

The invention encompasses modified immune cells including T cells expressing chimeric antigen receptors (CARs) and T cells modified through altering the specificity of the T cell receptor (TCRs) targeting TAAs, particularly those detailed herein. Modified TCRs, and CARs and immune cells expressing them, can be produced using routine techniques in the art, for example, those set forth in U.S. Pat. Nos. 8,088,379, 8,785,601, 5,359,046 and 8,389,282, which are hereby incorporated by reference.

In a preferred embodiment, the modified immune cell expresses a chimeric antigen receptor (CAR) or a TCR directed against CD19, melanoma-associated antigen recognized by T cells 1 (MART-1), glycoprotein (gp) 100, carcinoembryonic antigen (CEA), p53, MAGE-A3, or New York esophageal squamous cell carcinoma antigen (NY-ESO-1).

In preferred embodiments, the modified immune cell expresses a chimeric antigen receptor (CAR) or a TCR directed against folate receptor (FR) (preferably in ovarian cancer), carbonic anhydrase IX (CAIX) (preferably in renal cell carcinoma), L1-cell adhesion molecule (L1-CAM; CD171), CD20 (preferably in indolent non-Hodgkin lymphoma), and diasialoganglioside GD2 (preferably in neuroblastoma).

In preferred embodiments, the modified immune cell expresses a chimeric antigen receptor (CAR) or a TCR directed against CD19, HER-2, or CEA.

Preferably, the CAR comprises a single chain antibody, preferably a humanized scFv or an scFv derived from a human monoclonal antibody, directed against a TSA or TAA.

In a preferred embodiment, the immune cell has been modified with a vector, particularly a plasmid, a poxvirus, an adenovirus, an adeno-associated virus, an integrative or non-integrative lentivirus, or a measles virus vector. In a particularly preferred embodiment, the lentivirus technology set forth in U.S. Pat. No. 8,460,678 is used to construct the modified immune cell.

Cytokines

The invention encompasses the use of cyokines as anti-tumor compounds. Particularly preferred cytokines include interleukin or interferon. Particularly preferred cytokines are GM-CSF, Interleukin 12 (IL-12), IL-2, interferon-alpha2b, and IFN-gamma.

Anti-Angiogenic Therapies

The invention encompasses the use of anti-angiogenic compounds as anti-tumor compounds.

Compounds that inhibit vascular endothelial growth factor (VEGF) binding to its receptor can inhibit angiogenesis and consequently inhibit the formation of new blood vessels in tumors. A preferred anti-angiogenic compound is bevacizumab (brand name Avastin).

Other preferred anti-angiogenic compounds include kinase inhibitors that inhibit receptors, such as VEGFR which play a role in both tumor angiogenesis and tumor cell proliferation. Preferred kinase inhibitors include sorafenib, sunitinib, pazopanib, everolimus.

Other preferred anti-angiogenic compounds include itraconazole, carboxyamidotriazole, TNP-470 (an analog of fumagillin), CM101 (Group B *Streptococcus* toxin or ZD0101)), Interferon alpha (IFN-α), IL-12, platelet factor-4, suramin, thrombospondin, VEGFR antagonists, angiostatic steroids with heparin, Cartilage-Derived Angiogenesis Inhibitory Factor, matrix metalloproteinase inhibitors, angiostatin, endostatin, 2-methoxyestradiol, tecogalan, tetrathiomolybdate, thalidomide, thrombospondin, prolactin, αVβ3 inhibitors, linomide, tasquinimod, and ranibizumab.

Immune Checkpoint Blockade Molecule

In various embodiments, the invention encompasses using an immune checkpoint blockade molecule, preferably a monoclonal antibody, which targets, CTLA-4, PD-L1 or PD-1, as anti-tumor compound.

In various embodiments, the anti-tumor compound comprises a monoclonal antibody that targets CD27, CD28, CD40, CD122, CD137, B7-H3, B7-H4, A2R2, ICOS, VISTA, B7-H3, KIR, IDO, BTLA, GITR, OX40, LAG-3 or TIM-3/Tim-3L.

In some embodiments, the anti-tumor compound comprises multiple antibodies, including combinations of 2 or 3 antibodies targeted against CD27, CD28, CD40, CD122, CD137, B7-H3, B7-H4, A2R2, ICOS, VISTA, B7-H3, KIR, IDO, BTLA, CTLA-4, PD-L1, PD-1, GITR, OX40, LAG-3 or TIM-3/Tim-3L. In a preferred embodiment, the anti-tumor compound comprises antibodies targeting PD-1 and LAG-3.

In preferred embodiments, the monoclonal antibody is NIVOLUMAB, an IgG4 anti-PD-1 monoclonal antibody that acts as an immunomodulator by blocking ligand activation of the programmed cell death 1 (PD-1) receptor on activated T cells. Preferably, it is used for patients with metastatic melanoma or for the treatment of squamous non-small cell lung cancer.

PEMBROLIZUMAB is a humanized monoclonal antibody that targets the programmed cell death 1 (PD-1) receptor. Preferably, it is for use following treatment with IPILIMUMAB, or after treatment with IPILIMUMAB and a Serine/threonine protein kinase B-raf (BRAF) inhibitor in advanced melanoma patients who carry a BRAF mutation.

Virus and Nucleic Acid Vectors

In another embodiment, a vector expressing an antigen such as one of the antigens described above is used as an anti-tumor compound.

In a preferred embodiment, the vector is a plasmid vector.

Vectors are well-known in the art and include measles virus, lentivirus, retrovirus, adenovirus, poxvirus, herpes virus, measles virus, foamy virus or adeno-associated virus (AAV). Viral vectors can be replication-competent, or can be genetically disabled so as to be replication-defective or replication-impaired. Suitable vectors can be integrative or non-integrative.

In one embodiment, the vector is an Alphavirus vector. Alphaviruses are single-stranded positive-sense RNA viruses that replicate in the cytoplasm of infected cells. In various embodiments, the vector is a Venezuelan equine encephalitis virus (VEE), Sindbis virus (SIN), Semliki forest virus (SFV), and VEE-SIN chimera vector.

In various embodiments, the vector is a poxvirus, preferably a vaccinia virus, vector. In one embodiment, the poxvirus vector expresses a tumor antigen, such as prostate-specific antigen (PSA) or CEA, and multiple human T-cell co-stimulatory molecules (B7.1, LFA-3, and intracellular adhesion molecule-1). In various embodiments, the poxvirus vector is a replicating poxviral vector selected from attenuated modified vaccinia virus Ankara (MVA), NYVAC (derived from the Copenhagen strain of vaccinia), and ALVAC (canarypoxviral vector) strains.

In various embodiments, the vector is a lentiviral vector. Preferred vectors are the DNA Flap vectors as described in WO 99/055892, U.S. Pat. No. 6,682,507 and WO 01/27300, and U.S. Pat. No. 8,460,678, which are hereby incorporated by reference.

In a preferred embodiment, the virus expresses a 5T4 tumor-associated antigen. The nucleic acid vector can be an mRNA. Preferable, the mRNA is a modified mRNA, preferably in a nanoparticle. See, e.g., U.S. Pat. Nos. 8,664,194, 8,754,062, and 8,999,380, which are hereby incorporated by reference.

In one embodiment, an oncolytic adenovirus is used as an anti-tumor compound. Preferably, the oncolytic adenovirus is an adenovirus mutant lacking the E1B55 kDa gene (e.g., dl1520/ONYX-015) that can replicate selectively in p53 deficient cells. Preferably, the oncolytic adenovirus is Oncorine H101.

Chemotherapy Compounds

In some embodiments, the anti-tumor compound is a chemotherapy compound. Chemotherapy compounds include but not limited to alkylating agents (ex: cyclophosphamide), antimetabolites (ex: 5-fluorouracil, Gemcitabine, methotrexate), anti-tumor antibiotics (ex: doxorubicin, bleomycin, mitomycin-C), topoisomerase inhibitors (ex: etoposide, irinotecan), and mitotic inhibitors (ex: paclitaxel, vincristine, vinblastine)

In some embodiments, the chemotherapy compound is selected from 2,2',2"trichlorotriethylamine, 6-azauridine, 6-diazo-5-oxo-L-norleucine, 6-mercaptopurine, aceglarone, aclacinomycinsa actinomycin, altretamine, aminoglutethimide, aminoglutethimide, amsacrine, anastrozole, ancitabine, angiogenin antisense oligonucleotide, anthramycin, azacitidine, azaserine, aziridine, batimastar, bcl-2 antisense oligonucleotide, benzodepa, bicalutamide, bisantrene, bleomycin, buserelin, busulfan, cactinomycin, calusterone, carboplatin, carboquone, carmofur, carmustine, carubicin, carzinophilin, chlorambucil, chloraphazine, chlormadinone acetate, chlorozotocin, chromomycins, cisplatin, cladribine, cyclophosphamide, cytarabine, dacarbazine, dactinomycin, daunorubicin, defosfamide, demecolcine, denopterin, diaziquone, docetaxel, doxifluridine, doxorubicin, droloxifene, dromostanolone, edatrexate, eflornithine, elliptinium acetate, emitefur, enocitabune, epirubicin, epitiostanol, estramustine, etoglucid, etoposide, fadrozole, fenretinide, floxuridine, fludarabine, fluorouracil, flutamide, folinic acid, formestane, fosfestrol, fotemustine, gallium nitrate, gemcitabine, goserelin, hexestrol, hydroxyurea, idarubicin, ifosfamide, improsulfan, interferon-alpha, interferon-beta, interferon-gamma, interleukin-2, L-asparaginase, lentinan, letrozole, leuprolide, lomustine, lonidamine, mannomustine, mechlorethamine, mechlorethamine oxide hydrochloride, medroxyprogesterone, megestrol acetate, melengestrol, melphalan, menogaril, mepitiostane, methotrexate, meturedepa, miboplatin, miltefosine, mitobronitol, mitoguazone, mitolactol, mitomycins, mitotane, mitoxantrone, mopidamol, mycophenolic acid, nilutamide, nimustine, nitracine, nogalamycin, novembichin, olivomycins, oxaliplatin, paclitaxel, pentostain, peplomycin, perfosfamide, phenamet, phenesterine, pipobroman, pipsulfan, pirarubicin, piritrexim, plicamycin, podophyllinic acid 2-ethyl-hydrazide, polyestradiol phosphate, porfimer sodium, porfiromycin, prednimustine, procabazine, propagermanium, PSK, pteropterin, puromycin, ranimustine, razoxane, roquinimex, sizofican, sobuzoxane, spirogermanium, streptonigrin, streptozocin, tamoxifen, tegafur, temozolomide, teniposide, tenuzonic acid, testolacone, thiamiprine, thioguanine, Tomudex, topotecan, toremifene, triaziquone, triethylenemelamine, triethylenephosphoramide, triethylenethiophosphoramide, trilostane, trimetrexate, triptorelin, trofosfamide, trontecan, tubercidin, ubenimex, uracil mustard, uredepa, urethan, vinblastine, vincristine, zinostatin, and zorubicin, cytosine arabinoside, gemtuzumab, thioepa, cyclothosphamide, antimetabolites (e.g., methotrexate, 6-mercaptopurine, 6-thioguanine, cytarabine, 5-fluorouracil, fludarabine, gemcitabine, dacarbazine, temozoamide), hexamethylmelamine, LYSODREN, nucleoside analogues, plant alkaloids (e.g., Taxol, paclitaxel, camptothecin, topotecan, irinotecan (CAMPTOSAR, CPT-11), vincristine, vinca alkyloids such as vinblastine.) podophyllotoxin, epipodophyllotoxin, VP-16 (etoposide), cytochalasin B, gramicidin D, ethidium bromide, emetine, anthracyclines (e.g., daunorubicin), doxorubicin liposomal, dihydroxyanthracindione, mithramycin, actinomycin D, aldesleukin, allutamine, biaomycin, capecitabine, carboplain, chlorabusin, cyclarabine, daclinomycin, floxuridhe, lauprolide acetate, levamisole, lomusline, mercaptopurino, mesna, mitolanc, pegaspergase, pentoslatin, picamycin, riuxlmab, campath-1, straplozocin, tretinoin, VEGF antisense oligonucleotide, vindesine, and vinorelbine.

Compositions comprising one or more cancer therapeutics (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone. For a full listing of cancer therapeutics known in the art, see, e.g., the latest editions of The Merck Index and the Physician's Desk Reference. Likewise, the ADAM12 inhibitor of the invention may be used in conjunction with radiation therapy or other known cancer therapeutic modalities.

Methods for Treating a Cancer Patient

The invention encompasses methods for treating a cancer patient and for enhancing anti-tumor immune responses in a patient. In one embodiment, the invention encompasses a method comprising administering to the patient a combination of an ADAM12 inhibitor and an anti-tumor compound.

Similarly, the invention encompasses an ADAM12 inhibitor and an anti-tumor compound for use in treating a cancer patient. The invention further encompasses the use of an ADAM12 inhibitor and an anti-tumor compound for treating a cancer patient. The invention further encompasses the use of an ADAM12 inhibitor and an anti-tumor compound for the preparation of a medicament for treating a cancer patient.

The administration can be by conventional means including intravenous, oral, intramuscular, intratumoral, subcutaneous, and intranasal administration. A different form of administration may be used for the ADAM12 inhibitor and the anti-tumor compound.

Tumors that can benefit from adjuvant therapy anti-ADAM12+ cells include melanoma, prostate cancer, kidney cancer, breast cancer, colon cancer, pancreatic cancer, lung cancer, liver cancer, ovarian cancer, gastric cancer, bladder cancer and fibromatosis.

In other embodiments, the cancer is selected from the group consisting of prostate cancer, colorectal cancer, multiple myeloma, and non-small cell lung cancer. In certain other embodiments, the cancer is selected from lung cancer, colorectal cancer, breast cancer, pancreatic cancer and prostate cancer. Preferably, the cancer is selected from melanoma, colorectal carcinoma, synovial sarcoma, prostate cancer, breast cancer, lung cancer, and pancreatic cancer. Most preferably, the cancer is metastatic.

Dosages of compounds are routine in the art. Normally, the amount of ADAM12 inhibitor will be between 1-2000 mg, preferably between 1-800, 1-600, 1-400, 1-200, and 1-100 mg. This can be provided in a single dose or in multiple doses (e.g., 2, 3, 4 doses/day). In some embodiments, the ADAM12 inhibitor is administered at 1, 5, 10, 20, 30, 40, 50, 100, or 200 mg to 50, 100, 200, 400, 600, 800, 1500, and 2000 mg.

Preferably, the ADAM12 inhibitor is administered at between 1-50 mg/kg. Most preferably, the ADAM12 inhibitor is administered at 1, 2, 3, 4, 5, 6, 7, 8, 9, 10 to 4, 6, 8, 10, 12, 14, 16, 18, or 20 mg/kg.

In some embodiments, the invention encompasses a method comprising depleting ADAM12+ cells in a cancer patient and subsequently administering an anti-tumor compound or therapy to the patient. Preferably, the depletion of ADAM12+ cells is performed by administering an ADAM12 inhibitor, preferably an immunoconjugate, to the patient. In some embodiments, the method comprises administering an ADAM12 inhibitor, preferably an immunoconjugate, to the patient, and subsequently administering radiation therapy.

In some embodiments, the invention encompasses a method comprising treating a cancer patient with a first anti-tumor compound or therapy, measuring a lack of effectiveness of the first anti-tumor compound or therapy, and subsequently administering an ADAM12 inhibitor and a second anti-tumor compound or therapy to the patient. The lack of effectiveness of the first anti-tumor compound or therapy can be determined by methods known in the art, such as by measuring the size of the tumor at multiple timepoints, for example, using Magnetic Resonance Imaging (MRI), Computerized tomography (CT), ultrasound, mammogram, x-ray, etc.

In some embodiments, the invention encompasses a method comprising measuring the size of the tumor, treating a cancer patient with a first anti-tumor compound or therapy, measuring the size of the tumor after the first anti-tumor compound or therapy, and subsequently administering an ADAM12 inhibitor and a second anti-tumor compound or therapy to the patient.

Preferably, the ADAM12 inhibitor is an immunoconjugate. In some embodiments, the first and second first anti-tumor compound or therapy are the same. In some embodiments, the first and second anti-tumor compound or therapy are different. The first and second anti-tumor compound or therapy include all of the anti-tumor compounds and therapies detailed herein as if individually recited.

In preferred embodiments, the ADAM12 inhibitor, preferably an immunoconjugate, is administered after the first anti-tumor compound or therapy and before the second anti-tumor compound or therapy.

EXAMPLES

Example 1. Mice

Generation of ADAM12-GFP mice (M12-GFP) and ADAM12-DTR (M12-DTR) mice. The coding sequence for cre-Ires-egfp, or for tta-Ires-dtr including the stop codon and poly A sequence, was inserted into the exon 1 of the Adam12 mouse gene in place of the endogenous ATG translation start codon, on a 200 kb BAC (Invitrogen) carrying 80 kb of sequence upstream of the Adam12 translation start site. After modification of the ADAM12 BAC in vitro by homologous recombination, ADAM12-GFP or ADAM12-DTR BAC containing the inserted sequences were purified and injected into fertilized eggs implanted into foster mothers (Sparwasser et al., 2004). To induce neuroendocrine pancreatic tumors, RIP-Tag2 mice that express SV40 under control of the insulin promotor (Hanahan, D. *Nature* 315, 115-122 (1985)), were crossed to M12-DTR mice. All mice were kept in specific pathogen-free conditions and animal experiments were approved by the committee on animal experimentation of the Institut Pasteur and by the French Ministry of Agriculture.

Example 2. Mice Treatment

Mice were anaesthetized by ip injection of Xylazine/Ketamine and injected $5\times10^5$ murine melanoma cells (MO5) subcutaneously in the flank. ADAM12+ CAFs growing in melanoma were depleted by injecting diphtheria toxin intraperitoneal (ip) in the M12-DTR mice starting at day 9-10 after melanoma cells inoculation. At day 17 or 19, tumors were removed and processed for histology or FACS analysis. To measure tumor perfusion, 20 µl of Hoechst 33342 was injected intravenous (iv) 5-10 minutes before sacrifice.

Example 3. RNA Isolation and qPCR

Cells were FACS-sorted into vials containing RLT buffer (Qiagen) supplemented with β-mercaptoethanol, and total RNA was extracted using RNeasy Micro Kit (Qiagen). The quality of total RNA was assessed using the 2100 Bioanalyzer system (Agilent Technologies). 250-500 pg of high quality total RNA was subjected to one linear mRNA amplification cycle using the MessageBooster Kit for qRT-PCR (Epicentre Biotechnologies). 50-100 ng of amplified mRNA was transcribed into cDNA using Superscript III reverse transcriptase (Invitrogen). All procedures were performed according to the manufacturer's protocols. Quantitative real time PCR was performed using $RT^2$ qPCR primer sets and $RT^2$ SYBR-Green master mix (SABiosciences) on a PTC-200 thermocycler equipped with a Chromo4 detector (Bio-Rad Laboratories). Data were analyzed using Opticon Monitor software (Bio-Rad Laboratories). Ct values were normalized to the mean Ct values obtained for the two house-keeping genes Hsp90 and Gapdh.

Example 4. Histology

Tissue processing and staining procedures for immunofluorescence have been described previously (Peduto, L., et al., *J. Immunol.* 182, 5789-5799. (2009)). Briefly, tissues were fixed O/N at 4° C. in 4% paraformaldehyde (PFA) (Sigma), washed O/N in PBS, incubated in a solution of 30% sucrose (Sigma) until the samples sank, embedded in OCT compound 4583 (Sakura Finetek), frozen in a bath of isopentane cooled with liquid nitrogen and stocked at −80° C. Frozen blocs were cut at 8 µm thickness and sections were processed for staining: after blocking with 10% bovine serum in PBS containing 1% Triton (PBS-XG) for 1 hour at room temperature (RT), slides were incubated with primary antibodies (Abs) in PBS-XG overnight at 4° C., washed 3 times 5 min with PBS-XG, incubated with secondary conjugated Abs or streptavidin for 1 hour at RT, washed once, incubated with 4'6-diamidino-2-phenylindole-2HCl (DAPI) (Sigma) 5 min at RT, washed 3 times 5 min and mounted with Fluoromount-G (Southern Biotechnology Associates). Slides were examined with an AxioImager M1 fluorescence microscope (Zeiss) equipped with a CCD camera and images were processed with AxioVision software (Zeiss). Mosaic images were generated using Spinning Disk Confocal microscopy (Cell Voyager) and images were analysed with ImageJ software.

Example 5. Cells Isolation and FACS

To isolate stromal cells, tumors were removed and washed with PBS (Ca/Mg free), cut into 1 mm pieces and incubated at 37° C. for 30 min in a digestion solution composed of DMEM (Gibco), 0.5 mg/ml collagenase D (Roche), 0.13 U/ml Liberase TL (Roche) and 1 U/ml DNase 1 (Invitrogen). After 30 minutes, the digested fraction of the mix was collected and centrifuged in DMEM 10% FCS. Remaining undigested tissues were subjected to 1 or 2 additional cycles of digestion, collected and pressed through a 100-µm mesh. For FACS staining, cells were first pre-incubated with mAb 2.4G2 to block Fcγ receptors, and then incubated with the indicated Abs for 40 min in a total volume of 100 µl of PBS containing 2 mM EDTA and 2% bovine serum (PBS-F), followed by appropriate secondary Abs for 30 min when necessary, centrifuged in 2 ml PBS-F and dissolved in 200 µl of PBS-F for FACS analysis. Cells were incubated for 1 min with 4'6-diamidino-2-phenylindole-2HCl (DAPI) (Sigma) prior to analysis to exclude dead cells. Cell doublets were systematically excluded during analysis. Cells were analyzed with Fortessa (BD Biosciences) or Cyan ADP (Beckman Coulter), and Flowjo software (Tristar). Cells were sorted with FACS Aria 3 (BD Biosciences) to 95-98% purity.

Example 6. Antibodies

Antibodies that were purchased from BD Biosciences are: APC conjugated anti-CD31 (MEC 13.3), v500 conjugated anti-CD4 (RM4-5), FITC or PE-CF594 conjugated Mouse anti-CD45 (104 or 30-F11), purified Hamster anti-CD3e (500A2), Ly6C-BV605 (AL-21). Antibodies that were purchased from Invitrogen are: purified rabbit anti-GFP (A-11122) and FITC-conjugated anti-rabbit polyclonal. Antibodies that were purchased from eBioscience are: PE conjugated anti-CD8 (CT-CD8b), PE conjugated anti-CD3e (145-2C11), eF450 conjugated anti-CD25 (PC61.5), APC conjugated anti-CD11b (M1/70), Biotin conjugated anti-CD11c (N418), F4/80-Pecy7 (BM8). Antibodies that were purchased from Invitrogen MP are: Alexa 647, Alexa 488, or PercpCy5.5-conjugated streptavidins. Antibodies that were purchased from Jackson Lab are: Cy3 conjugated anti-Syrian Hamster. Antibodies that were purchased from Biolegend are: CD206-PE (C068C2). gp38 serum was a gift of A. Farr.

Example 7. ADAM12+ CAFs Develop in the Tumor Stroma of a Murine Melanoma

ADAM12 is not expressed at homeostasis in adult organs. To determine whether tumorigenesis in a murine melanoma model induce the development of ADAM12+ CAFs, melanoma cells were injected subcutaneously in the ADAM12-GFP mice. At 10-12 days, development of ADAM12+ cells in the tumor stroma at the peripheral margins of the tumor was observed (FIG. 1A). This region is usually dense in stromal cells-CAFs, collagen, vessels and immune cells. ADAM12+ cells were identified by FACS at day 8-10 as PDGFRα+ CAFs (FIG. 1B)

Example 8. ADAM12+ CAFs Express Pro-Inflammatory Cytokines and Chemokines

Chemokines play an essential role in leucocyte recruitment into the tumor. In addition, tumor angiogenesis, which is regulated by pro-angiogenic factors such as VEGF, may also affect leucocyte recruitment. To determine whether ADAM12+ CAFs have a role in these processes, ADAM12+ and ADAM12– CAFs were isolated by FACS from melanoma. Total RNA was extracted from these different subsets of stromal cells, and transcripts expression was analysed by using quantitative reverse-transcriptase (qRT)-PCR. ADAM12+ CAFs expressed higher levels of transcripts for the chemokines CXCL10 and CXCL12, which have essential roles in T cell recruitment, as well as the pro-inflammatory cytokine IL6, as compared to ADAM12– CAFs. In addition, ADAM12+ CAFs expressed high levels of the pro-angiogenic factor VEGFa, as well as transcript coding for type I collagen, an essential constituent of the tumor extracellular matrix (FIG. 2). These results show that ADAM12+ CAFs are an immunomodulatory and proangiogenic subset of CAFs.

Example 9. Depletion of ADAM12+ CAFs Improves Vessel Density/Activation and Tumor Perfusion To determine the impact of ADAM12+ CAFs during tumor growth, melanoma cells were injected into M12-DTR mice, which carry the diphtheria toxin receptor (dtr) under control of the Adam12 gene. In these mice, ADAM12+ CAFs were specifically depleted by injecting diphtheria toxin (DT) starting when tumors were palpable at day 9 or 10. Two or three weeks after tumor inoculation, melanoma tumors were isolated and immunofluorescence analysis of the tumor vasculature was performed on frozen sections. Tumors lacking ADAM12+ CAFs (in M12-DTR+DT) had a higher density of CD31+ vessels inside the tumors. In addition, CD31+ vessels displayed an activated ICAM1+ phenotype, which is required for leucocyte adhesion and further extravasation (FIG. 3A). Tumors lacking ADAM12+ CAFs had increased perfusion, as determined by measuring the positive area of staining obtained after injection with the DNA binding Hoechst 33342 (FIG. 3B). Similar results were obtained in RIP-Tag2 mouse model for neuroendocrine pancreatic tumor (FIG. 3C-D).

Figure 5:
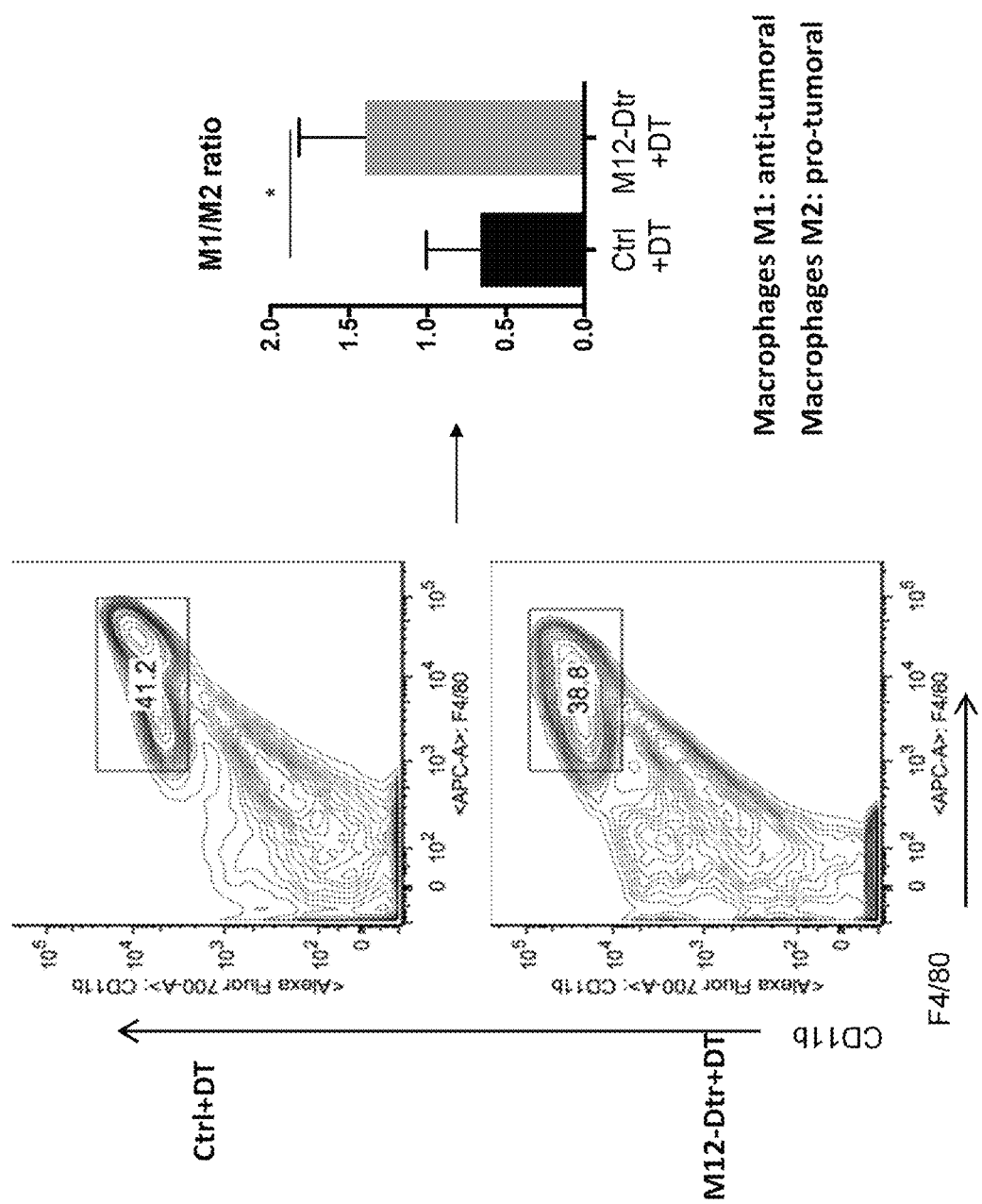
FIG. 5: In melanoma mice model tumors lacking ADAM12+ stromal cells (in M12-DTR mice injected with DT-diphteria toxin) have increased ratio of M1/M2 macrophages.

Example 10. Depletion of ADAM12+ CAFs Improves T Cells Infiltration Inside the Tumor, Promotes M1 Macrophages, and Limits Tumor Growth Adaptive immunity is essential for tumor control. In large tumors, even though cytotoxic T cells are recruited to the tumor, they often concentrate in the stromal capsule at the periphery of the tumor. After injection of DT, tumors lacking ADAM12+ CAFs displayed significantly higher frequency of CD3+ T cells compared to tumors with normal stroma (FIG. 4A, right panel). While the percentage of other immune populations such as myeloid-derived suppressor cells (MDSC), and T-regulator cells (Tregs) remained unchanged, the ratio of M1/M2 macrophages was increased, favoring anti-tumoral M1 macrophages (FIG. 5). In addition, CD3+ T cells were now recruited to the core of the tumor, in contrast to tumors harboring a normal tumor stroma (FIG. 4A, left panel). In these settings, tumor growth was significantly delayed in the murine melanoma model when ADAM12+ CAFs were depleted, compared to mice with a normal tumor stroma (FIG. 4B).

The invention claimed is:

1. A method of treating a cancer in a patient, comprising administering to the patient a composition, or combination of compositions, comprising a second anti-tumor compound, and an ADAM12 inhibitor which is an immunoconjugate that depletes ADAM12 expressing cells,
    wherein the patient has undergone a previous treatment of a tumor with a first anti-tumor compound or therapy that was measured as lacking effectiveness,
    wherein the immunoconjugate comprises a monoclonal antibody or antibody fragment thereof that binds ADAM12 on the surface of cells and a toxin, and
    wherein administering the ADAM12 inhibitor to the patient depletes ADAM 12 expressing stromal cells of the tumor stromal capsule, which improves the vasculature, tumor perfusion and CD3+ T cells infiltration in the central region of the tumor, and thereby increases the effectiveness treatment of the tumor with the second anti-tumor compound compared to previous treatment of the tumor with the first anti-tumor compound or therapy that was measured as lacking effectiveness, and
    wherein the cancer is selected from the group consisting of melanoma, prostate cancer, and pancreatic cancer.

2. The method of claim 1, wherein the first and second anti-tumor compounds are the same.

3. The method of claim 1, wherein the first and second anti-tumor compounds are different.

4. The method of claim 1, wherein administering the composition, or combination of compositions, to the patient enhances an anti-tumor immune response in the patient.

5. The method of claim 1, wherein the second and/or first anti-tumor compounds are selected from the group consisting of: a Tumor-Specific Antigen (TSA), a Tumor-Associated Antigen (TAA), an antibody, a modified immune cell, a cytokine, an immune checkpoint blockade molecule, a virus or nucleic acid vector, a chemotherapy drug, and an anti-angiogenic drug.

6. The method of claim 5, wherein the Tumor-Specific Antigen (TSA) or Tumor-Associated Antigen (TAA) is selected from the group consisting of: MAG-Tn3, MAGE-A3, New York esophageal squamous cell carcinoma antigen (NY-ESO-1), HER-2/neu, p53, melanoma-associated antigen recognized by T cells 1 (MART-1), glycoprotein (gp) 100, Alphafetoprotein (AFP), EGFRvIII-specific 14-amino acid peptide, PEP-3 chemically conjugated to keyhole limpet hemocyanin (KLH), CA-125, MUC-1, carcinoembryonic antigen (CEA), Epithelial tumor antigen (ETA), Tyrosinase, prostatic acid phosphatase (PAP), prostate-specific antigen (PSA), Sialyl-Tn, prostate specific membrane antigen (PSMA), and non-catalytic hTERT.

7. The method of claim 5, wherein the second and/or first anti-tumor compounds are an antibody, wherein the antibody is a monoclonal antibody that targets CD52, EGFR, VEGF, HER-2, CD20, CD16, OX40, CD137, CD27, GITR, CD40, CD19, CD272, CD279, CD274, PAP, CD38, CD47, or GD2.

8. The method of claim 5, wherein the modified immune cell is a dendritic cell.

9. The method of claim 8, wherein the dendritic cell expresses a PAP antigen.

10. The method of claim 5, wherein the modified immune cell is a T cell.

11. The method of claim 5, wherein the modified immune cell expresses a chimeric antigen receptor (CAR).

12. The method of claim 11, wherein the CAR is directed against CD19, melanoma-associated antigen recognized by T cells 1 (MART-1), glycoprotein (gp) 100, carcinoembryonic antigen (CEA), p53, MAGE-A3, or New York esophageal squamous cell carcinoma antigen (NY-ESO-1).

13. The method of claim 5, wherein the cytokine is an interferon or an interleukin.

14. The method of claim 5, wherein the immune checkpoint blockade molecule is a monoclonal antibody that targets CTLA-4, PD-L1, or PD-1.

15. The method of claim 5, wherein the virus expresses a 5T4 tumor-associated antigen.

16. The method of claim 1, wherein the administered composition, or combination of compositions further comprises a Dipeptidylpeptidase 4 (DPP4) inhibitor selected from the group consisting of: Sitagliptin, Vildagliptin, Saxagliptin, Linagliptin, Anagliptin, Teneligliptin, Alogliptin, Gemigliptin and Dutogliptin.

17. The method of claim 1, wherein the second anti-tumor compound and the ADAM12 inhibitor are administered sequentially.

18. The method of claim 1, which comprises administering a composition comprising the ADAM12 inhibitor to deplete stromal cells of the tumor stromal capsule, and subsequently administering a composition comprising the second-antitumor compound.

19. The method of claim 1, wherein the cancer is melanoma.

20. The method of claim 1, wherein the cancer is prostate cancer.

21. The method of claim 1, wherein the cancer is pancreatic cancer.

* * * * *